United States Patent
Tanoshima et al.

(10) Patent No.: US 8,663,557 B2
(45) Date of Patent: Mar. 4, 2014

(54) ANALYZER

(75) Inventors: Eiji Tanoshima, Kobe (JP); Yuuji Wakamiya, Kobe (JP)

(73) Assignee: Sysmex Corporation, Kobe (JP)

(*) Notice: Subject to any disclaimer, the term of this patent is extended or adjusted under 35 U.S.C. 154(b) by 1641 days.

(21) Appl. No.: 11/038,951

(22) Filed: Jan. 19, 2005

(65) Prior Publication Data

US 2005/0175504 A1  Aug. 11, 2005

(30) Foreign Application Priority Data

Jan. 20, 2004  (JP) .................................. 2004-012014

(51) Int. Cl.
*G01N 35/02* (2006.01)

(52) U.S. Cl.
USPC .................. 422/67; 422/62; 422/63; 422/65; 436/47; 436/48; 436/50

(58) Field of Classification Search
USPC .................................................. 436/47–50
See application file for complete search history.

(56) References Cited

U.S. PATENT DOCUMENTS

| | | | | |
|---|---|---|---|---|
| 4,451,433 A | * | 5/1984 | Yamashita et al. | 422/63 |
| 4,522,921 A | * | 6/1985 | Ogawa | 436/47 |
| 5,415,840 A | * | 5/1995 | Sano et al. | 422/67 |
| 6,060,022 A | * | 5/2000 | Pang et al. | 422/65 |
| 6,136,274 A | * | 10/2000 | Nova et al. | 506/33 |
| 6,410,278 B1 | | 6/2002 | Notomi et al. | |
| 6,709,634 B1 | | 3/2004 | Okada et al. | |
| 2005/0013735 A1 | * | 1/2005 | Gebrian et al. | 422/63 |
| 2005/0014285 A1 | * | 1/2005 | Miller | 436/180 |
| 2005/0123445 A1 | * | 6/2005 | Blecka et al. | 422/64 |
| 2005/0186113 A1 | * | 8/2005 | Koike et al. | 422/63 |
| 2006/0000296 A1 | * | 1/2006 | Salter | 73/863.01 |

FOREIGN PATENT DOCUMENTS

| | | |
|---|---|---|
| JP | 05-085491 A | 4/1993 |
| JP | H08-262034 | 10/1996 |
| JP | 09-072911 A | 3/1997 |
| JP | 10-019776 A | 1/1998 |
| JP | 2000-356575 A | 12/2000 |

* cited by examiner

*Primary Examiner* — Lyle Alexander
(74) *Attorney, Agent, or Firm* — Brinks Gilson & Lione (57) ABSTRACT

An analyzers that comprise a container holder for placing containers; a detector for detecting whether or not a container is placed at the container holder; a controller for acquiring the status of the container holder based on the output of the detector; and a display for displaying the status of the container holder is disclosed.

8 Claims, 8 Drawing Sheets

ANALYZER

This application claims priority under 35 U.S.C. §119 to Japanese Patent Application No. 2004-012014 filed Jan. 20, 2004, the entire content of which is hereby incorporated by reference.

FIELD OF THE INVENTION

The present invention relates to an analyzer, and specifically relates to an analyzer including a container holder for holding a container.

BACKGROUND

Conventional analyzers incorporating a container holder for installing containers are well known (for example, refer to Japanese Laid-Open Patent Publication No. H8-262034). Japanese Laid-Open Patent Publication No. H8-262034 discloses an autoanalyzer provided with a means for specifying a sample placement position by number before placement of the sample container when a sample container containing a sample is placed in a sample container holding unit. In this way the user can confirm the sample placement position before placement of the sample container.

Furthermore liquid sample analyzers which allow a user to manually place a detection cell in a detection unit are also known (for example, Japanese Laid-Open Patent Publication No. 2000-356575).

In the autoanalyzer disclosed in Japanese Laid-Open Patent Publication No. H8-262034, however, a problem arises insofar as it is not possible to confirm whether or not a sample container has actually been placed in the displayed sample placement position after the sample placement position has been displayed on the display.

Furthermore, in the liquid sample analyzer disclosed in Japanese Laid-Open Patent Publication No. 2000-356575, a problem arises insofar as it is difficult for a user to grasp how many detection containers should be placed in the detection unit when a single sample is to be assayed several times, and when several assays are to be performed.

SUMMARY

The scope of the present invention is defined solely by the appended claims, and is not affected to any degree by the statements within this summary.

An object of the present invention is to provide an analyzer having improved usability.

A first aspect of the present invention is an analyzer including a container holder for placing containers; a detector for detecting whether or not a container is placed at the container holder; a controller for acquiring the status of the container holder based on the output of the detector; and a display for displaying the status of the container holder.

A second aspect of the present invention is an analyzer including an input unit for inputting assay information relating to sample assays; a plurality of container placement positions for placing containers; a controller for determining a container placement position which is used based on the assay information input by the input unit; and a display for displaying the container placement position which is used graphically.

A third aspect of the present invention is an analyzer including a container placement position for placing a container; a light source for emitting light at the container placement position; a receiver for receiving the light emitted by the light source; and a controller for determining whether or not a container is placed in the container placement position based on the output of the receiver.

A fourth aspect of the present invention is an analyzer including an input unit for inputting assay information relating to sample assays; a plurality of container placement positions for placing the detection containers; a detector for detecting signals from the liquid contained in the detection container placed in the container placement position; a controller for calculating the number of detection containers to be used based on the assay information input by the input unit, and determining a container placement position to be used for detecting the signal from the liquid based on the calculated number; and a display for notifying the container placement position to be used.

DETAILED DESCRIPTION OF THE PREFERRED EMBODIMENTS

The preferred embodiments of the present invention are described hereinafter with reference to the drawings.

The present embodiment is described in terms of a gene amplification detection device. The gene amplification detection device is an analyzer aiding the diagnosis of cancer metastasis in surgically excised tissue; nucleic acids (mRNA) of cancerous origin present in the excised tissue are amplified using the LAMP (loop-mediated isothermal amplification) method, and the marker gene is detected by measuring the turbidity of the liquid generated in conjunction with the nucleic acid amplification. Details of the LAMP method are disclosed in U.S. Pat. No. 6,410,278.

Figure 1:
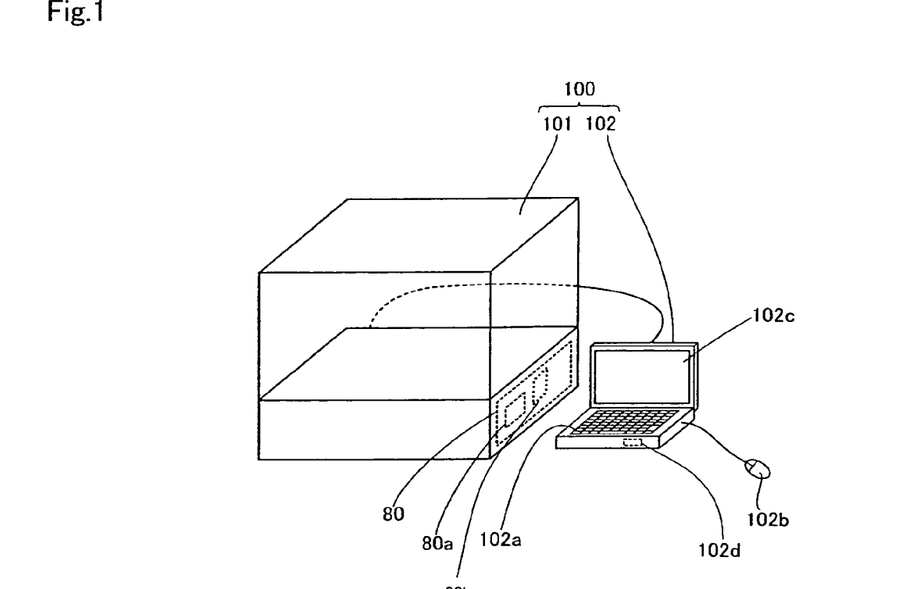
FIG. 1 is a perspective view showing the general structure of the gene amplification detection device and its data processing unit of an embodiment of the present invention
Figure 2:
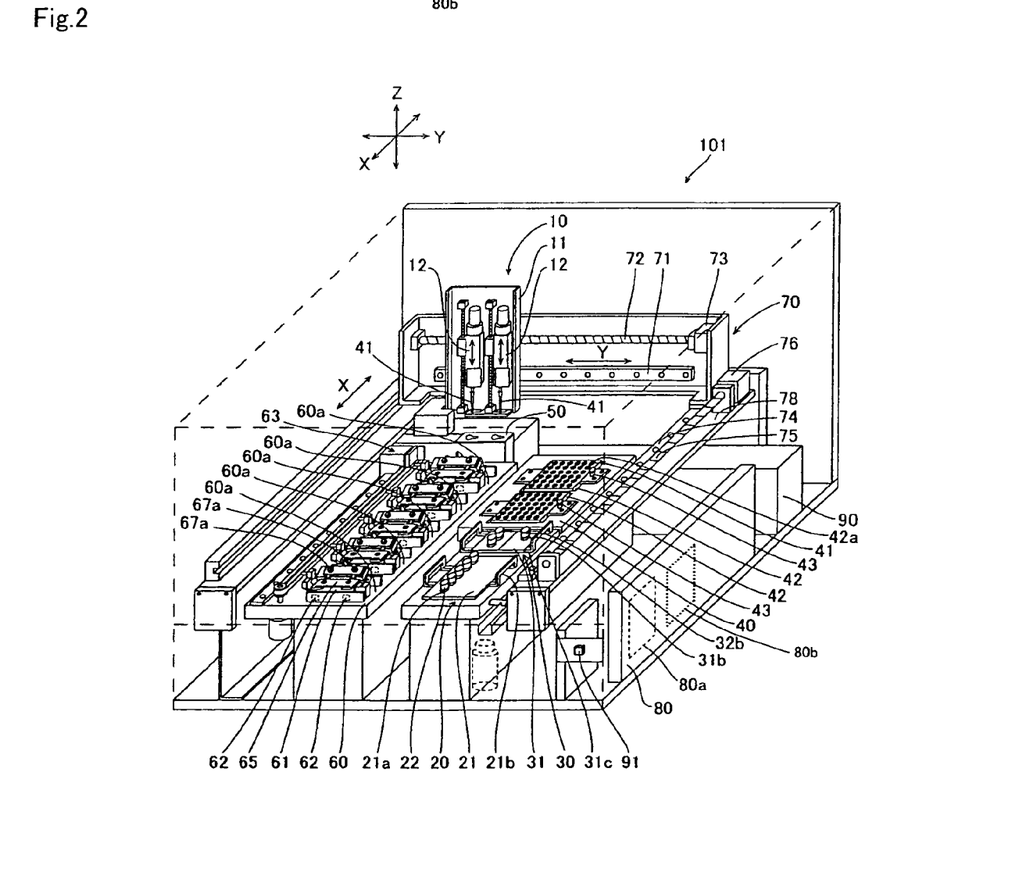
FIG. 2 is a perspective view showing the general structure of the assay unit of the gene amplification detection device shown in FIG. 1.

The overall structure of the gene amplification detection device and its data processing unit of the present embodiment are described with reference to FIGS. 1 and 2. As shown in FIG. 1, the gene amplification detection device 100 includes an assay unit 101, and a data processing unit 102 connected to the assay unit 101 by a communication line. The assay unit 101 includes a controller 80 which is provided with a CPU 80a and memory 80b, as shown in FIGS. 1 and 2. The controller 80 controls the operation of the assay unit 101, and controls the input and output between the assay unit 101 and external devices. The data processing unit 102 is a personal computer including a keyboard 102a, mouse 102b, display 102c, and controller 102d, as shown in FIG. 1. The controller 102d includes memories such as ROM and RAM and the like, and a CPU.

Figure 3:
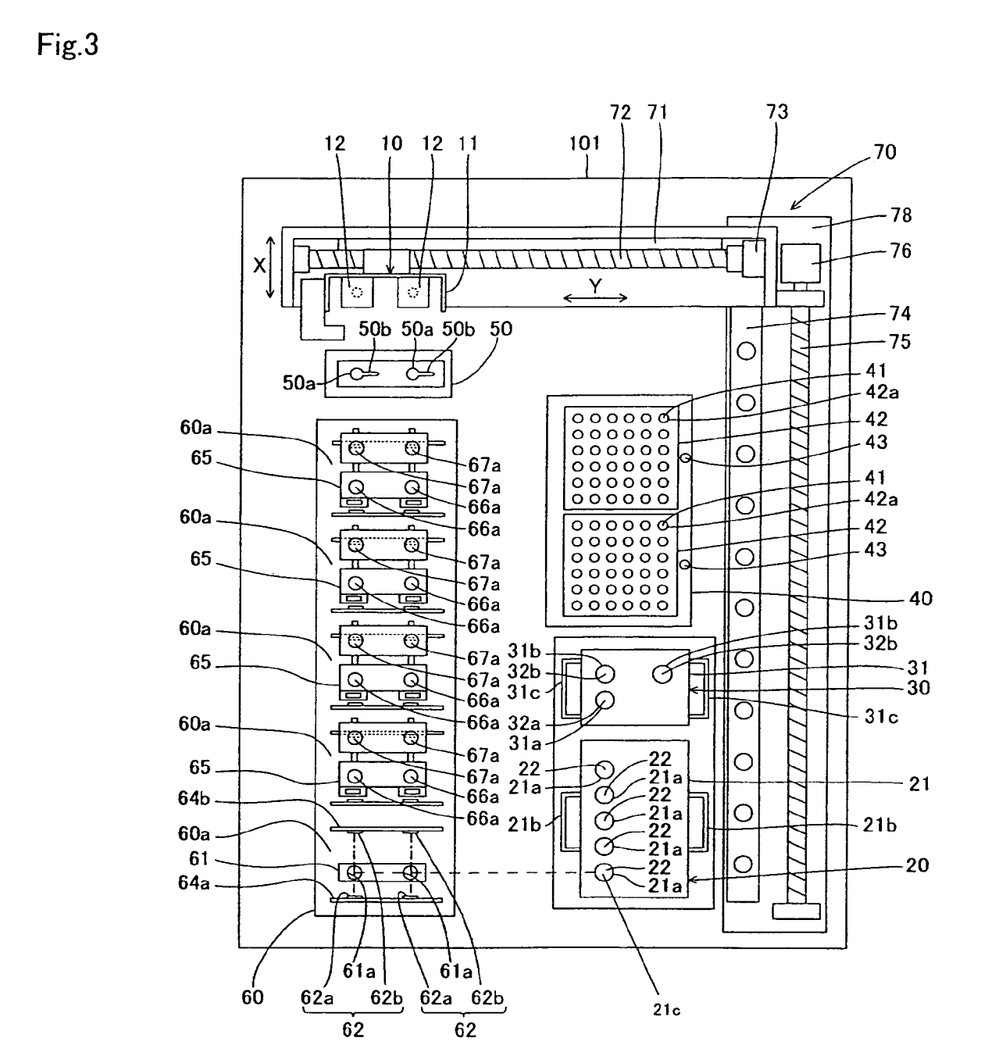
FIG. 3 is a brief top view of the assay unit of the gene amplification detection device shown in FIG. 1.

As shown in FIGS. 2 and 3, the assay unit 101 includes a dispensing mechanism 10, sample container holder 20, reagent container holder 30, tip holder 40, tip disposal unit 50, container holder 60 including five reaction detection blocks 60a, a cover closing mechanism 63, and a transfer unit 70 for moving the dispensing mechanism 10 in the X- and Y-axis directions. The assay unit 101 has an internal power source 90 for supplying power to the entire device including the controller 80. An emergency stop switch 91 is provided at a predetermined location on the front of the assay unit 101.

The dispensing mechanism 10 includes an arm 11 which is moved in the X-axis and Y-axis directions (horizontal directions) by the transfer unit 70, and two syringe units 12 which are respectively movable in the Z-axis direction (vertical direction) independent of the arm 11.

As shown in FIGS. 2 and 3, a sample container placement platform 21, which is provided with five sample container holes 21a and a handle 21b, is removably inserted in a concavity (not shown in the drawing) of the sample container holder 20. A microswitch 21c is assembled at the bottom of each of the five sample container holes 21a. The five microswitches 21c are OFF when a sample container 22 is not placed in the sample container hole 21a, and are ON when a sample container is placed in the sample container hole. The five microswitches 21c are respectively connected to the controller 80. The five sample container holes 21a are sequentially arranged from the inner side of the device as following: sample position 1, sample position 2, sample position 3, sample position 4, and sample position 5. Sample containers 22 which contain soluble extract (sample) prepared processing excised tissue (homogenizing, filtering, diluting) beforehand are placed in the five sample container holes 21a of the sample container placement platform 21. In the sample container holes 21a are also placed containers which contain a negative control for confirming normal non-amplification of genes which should not be amplified, and a positive control for confirming normal amplification of genes which should be amplified.

A reagent container placement platform 31, which includes two primer container holes 31a and one enzyme container hole 31b and a handle 31c, is removably inserted in a concavity (not shown in the drawing) of the reagent container holder 30. The primer reagent container holes 31a of the reagent container placement platform 31 are arranged along the Y-axis direction at predetermined spacing, and the enzyme reagent container hole 31b is provided only on the front left side. Primer reagent containers 32a containing cytokeratin 19 (CK19) and enzyme reagent container 32b containing both CH19 and β-actin are respectively placed in the primer reagent container hole 31a and enzyme reagent container hole 32b on the front left side. A primer reagent container 32 containing β-actin primer reagent is placed in the primer reagent container hole 31a on the front right side.

Two racks 42, which are provided with holes 42a for accommodating 36 pipette tips 41, are removably inserted in two concavities (not shown in the drawing) of the tip holder 40. Two detachment buttons 43 are provided on the tip holder 40. The racks 42 are put in a removable state by depressing the detachment buttons 43.

As shown in FIG. 3, two tip disposal holes 50a for disposing of used pipette tips 41 are provided in the tip disposal unit 50. A channel 50b having a width narrower than the tip disposal holes 50a is provided to connect the tip disposal holes 50a.

The five reaction detection blocks 60a of the container holder 60 respectively include reaction unit 61 and two turbidity detection units 62, as shown in FIG. 2. Two detection cell placement positions 61a for placing the transparent detection cell 65 are provided in each reaction unit 61, as shown in FIG. 3.

The detection cell 65 is a container for reacting sample and reagent. The detection cell 65 has two container parts for containing the sample and the reagent. Each container part is accommodated in the cell placement position 61a. A hole for accommodating the container part is provided in the detection cell placement position 61a. Each reaction detection block 60a is arranged sequentially from the inner side of the device as follows: cell position 1, cell position 2, cell position 3, cell position 4, cell position 5.

The turbidity detection unit 62 includes an LED light source 62a which is a blue color LED having a 465 nm wavelength and which mounted on a base plate 64a positioned on one side wall of the reaction unit 61, and a photodiode photoreceptor 62b mounted on a base plate 64b positioned on another side wall of the reaction unit 61. A set of turbidity detection units 62, which include one LED light source 62a and one photodiode photoreceptor 62b, are arranged in pairs in each reaction detection block 60a. Accordingly, a total of ten sets of turbidity detection units 62, which include LED light source 62a and photodiode photoreceptor 62b, are arranged in the five reaction detection blocks 60a. The LED light source 62 and its corresponding photodiode photoreceptor 62b are arranged such that the photodiode photoreceptor 62b is capable of receiving the approximately 1 mm diameter light beam emitted from the LED light source 62a at the bottom of the detection cell 65. The controller 80 determines whether or not a detection cell 65 is present based on the intensity of the light received by the photodiode photoreceptor 52b. Specifically, the light received by the photodiode photoreceptor 62b is attenuated when a detection cell 65 is disposed between the LED light source 62a and the photodiode photoreceptor 62b than when a detection cell 65 is not present. In this way the controller 80 is capable of determining when a detection cell 65 is placed. Furthermore, the controller 102d monitors in real time the turbidity of the liquid contained within the detection cell 65 by means of the intensity of the light received by the photodiode photoreceptor 62b.

As shown in FIGS. 2 and 3, the transfer unit 70 includes a direct-drive guide 71 and ball screw 72 for moving the dispensing mechanism 10 in the Y-axis direction, stepping motor 73 for driving the ball screw 72, and direct-drive guide 74 and ball screw 75 for moving the dispensing mechanism 10 in the X-axis direction, and stepping motor 76 for driving the ball screw 76. Moving the dispensing mechanism 10 in the X- and Y-axis directions is accomplished by rotating the ball screws 72 and 75 using the stepping motors 73 and 76, respectively.

The operation of the gene amplification detection device 100 of the present embodiment is described below with reference to FIGS. 1 through 8. The gene amplification detection device 100 is a device in which a plurality of detection cells 65 to be used are placed in the reaction detection block 60a by a user, then the assay operation is started according to the user directions, and when assay operation have been completed for all the placed detection cells 65, the used detection cells 65 are removed by the user.

As shown in FIGS. 2 and 3, a sample container 22, which contains a soluble extract liquid (sample) prepared beforehand by processing (homogenizing, filtering, diluting) excised tissue, is placed in the sample container hole 21a of the sample container platform 21. Then the user places the primer reagent container 32a containing CK19 (cytokeratin 19) and the enzyme reagent container 32b containing both CK19 and β-actin enzyme reagent in the front left side primer reagent container hole 31a and enzyme reagent container hole 31b (refer to FIG. 3). The user then places the primer reagent container 32a containing β-actin in the front right side primer reagent container hole 31a and enzyme reagent container hole 51b.

The user then inserts two racks 42 respectively holding 36 disposable pipette tips 41 in the concavities of the tip holder 40 (not shown in the drawings). In this case, since the initial position (origin position) of the arm 11 of the dispensing mechanism 10 is a distance above the tip holder 40, as shown in FIGS. 2 and 3, the two racks 42 can easily be placed in the concavities of the tip holder 40 (not shown in the drawings).

In the present embodiment, assay information relating to the assays of a sample such as assay item, an ID (identification information) for identifying a sample, the number of assays and the like are recorded on the screen of the display 102c of the data processing unit 102 using the keyboard 102a and mouse 102b of the data processing unit 102 shown in FIG. 1. Details of the recording of assay information are described below with reference to FIGS. 4 through 7. First, the layout of the screen of the display 102c of the data processing unit 102 is described referring to FIG. 4. This screen is provided with an order list display 122 for displaying the recording status of the assay information, batch number display 123, group list display 124 for selecting assay item, cell placement position displays 125a through 125e, sample placement position display 126, and assay start button 127.

Figure 4:
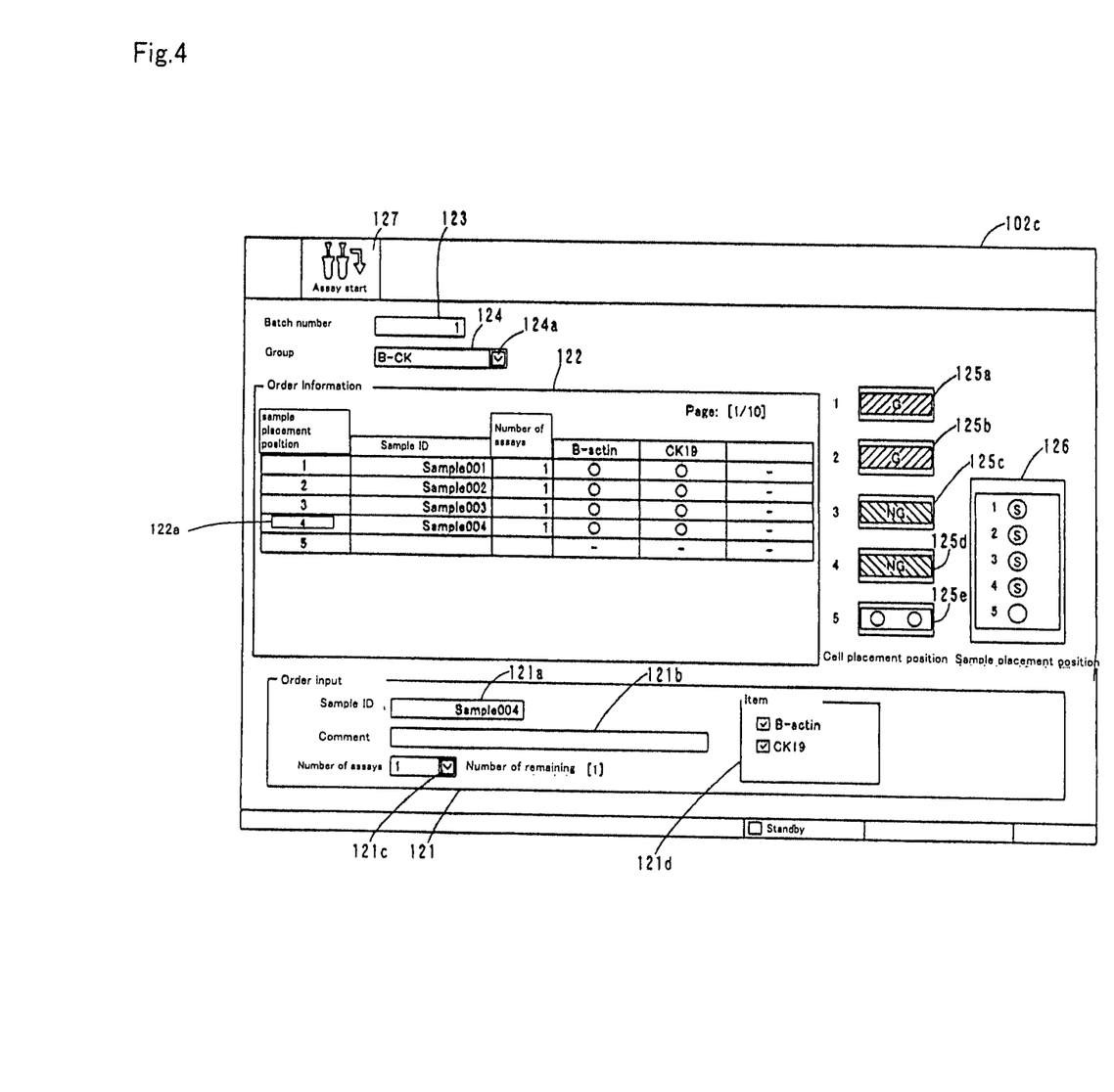
FIG. 4 illustrates the screen for receiving assay information which is displayed on the display of the data processing unit of the gene amplification detection device shown in FIG. 1.

First, assay information of the sample placement positions 1 through 5 is input to the order input unit 121 on the screen of the display 102c in the standby state shown in FIG. 4. The order input unit 121 displays a screen for recording the assay information of the sample placement position indicated by the cursor 122a. The ID for identifying the sample is input using the keyboard 102a. In addition to the biological material ID, ID representing negative control and positive control and the like may be entered as this ID. The biological material ID may be, for example, "sample 001~sample 005"; negative control ID may be "Neg"; and positive control ID may be "Pos." The example shown in FIG. 4 shows all input IDs are biological material IDs.

Comments are input in the comment input unit 121b of the order input unit 121 for each sample. Regarding the respective samples, the number of assays for a single sample is selected from a pull-down menu 121c of the order input unit 121. In the gene amplification detection device 100, [1] or [2] can be set as the number of assays; [1] is set as the number of assays for sample 004 in the example of FIG. 4. When the enter key is pressed on the keyboard 102a, the input ID and number of assays are stored in the memory of the controller 102d, and displayed on the order list display 122. The sample placement position display 126 displays from the top down sample position 1, sample position 2, sample position 3, sample position 4, sample position 5. An alphabetical letter ("S" in the present embodiment) corresponding to the top letter of the ID displayed on the order list display 122 is displayed on the sample placement position display 126. FIG. 4 shows a screen of sample placement position 4 after assay information has been input. When "Neg" is input as the ID, "N" is displayed, and when "Pos" is input as the ID, "P" is displayed on the sample placement position display 126. On the sample placement display 126, the sample placement position of an input ID is displayed with a green or red background depending on whether or not the sample container 22 is placed in the sample container hole (presence/absence of the sample container). In the example shown in FIG. 4, the backgrounds of the sample placement positions 1 through 4 are displayed in green or red. Accordingly, the position of the sample container hole 21a in which the sample container 22 is to be placed, and whether or not the sample container 22 is actually placed at this position can be confirmed by the user looking at the sample placement position display 126. The sample placement positions for which IDs are not input are displayed with a white background.

The number of the batch process is automatically displayed on the batch number display 123. The batch process is for performing the processing of a plurality of samples in a batch. That is, in a single batch process, the gene amplification detection device 100 starts the assay operation according to the user directions after the user has placed the plurality of detection cells 65 to be used in the reaction detection blocks 60a, and ends the assay operation for all the placed detection cells 65.

After the power supply is turned ON, the number resulting from adding [1] to the number of iterations of the batch process is displayed on the batch number display 123. In the group selection unit 124, a group is selected from the pull-down menu 124a. Selections for this group include group (B-CK) for assaying two assay item CK19 and β-actin, group (CK) for assaying only CK19, group (B) for assaying only β-actin, and group (Other) for assaying three assay item by adding one other assay item to the CK-a9 and β-actin. FIG. 4 shows an example when group (B-CK) is selected for assaying two item of CK19 and β-actin. By selecting the group (B-CK), the assay item CK19 and β-actin specified for the sample, which has its ID displayed on the order list display 122, is stored in the memory 102e, and a [O] symbol is displayed in the locations corresponding to CK19 and β-actin on the order list display 122.

It is also possible to not assay the assay item which have been unchecked among the CK19 and β-actin by unchecking the CK19 and β-actin separately for each individual sample in the item selection unit 121d of the order input unit 121 even when the group (B-CK) has been selected.

The cell placement position displays 125a through 125e show the status of the five reaction detection blocks 60a graphically. The cell placement position displays 125a through 125e correspond to the cell placement positions 1 through 5 of the reaction detection blocks 60a of the assay unit 101 the position of the reaction detection block 60a in which the detection cells 65 are to be placed, and whether or not the detection cells 65 are actually placed at these positions can be confirmed by the user glancing at the cell placement position displays 125a through 125e.

Figure 5:
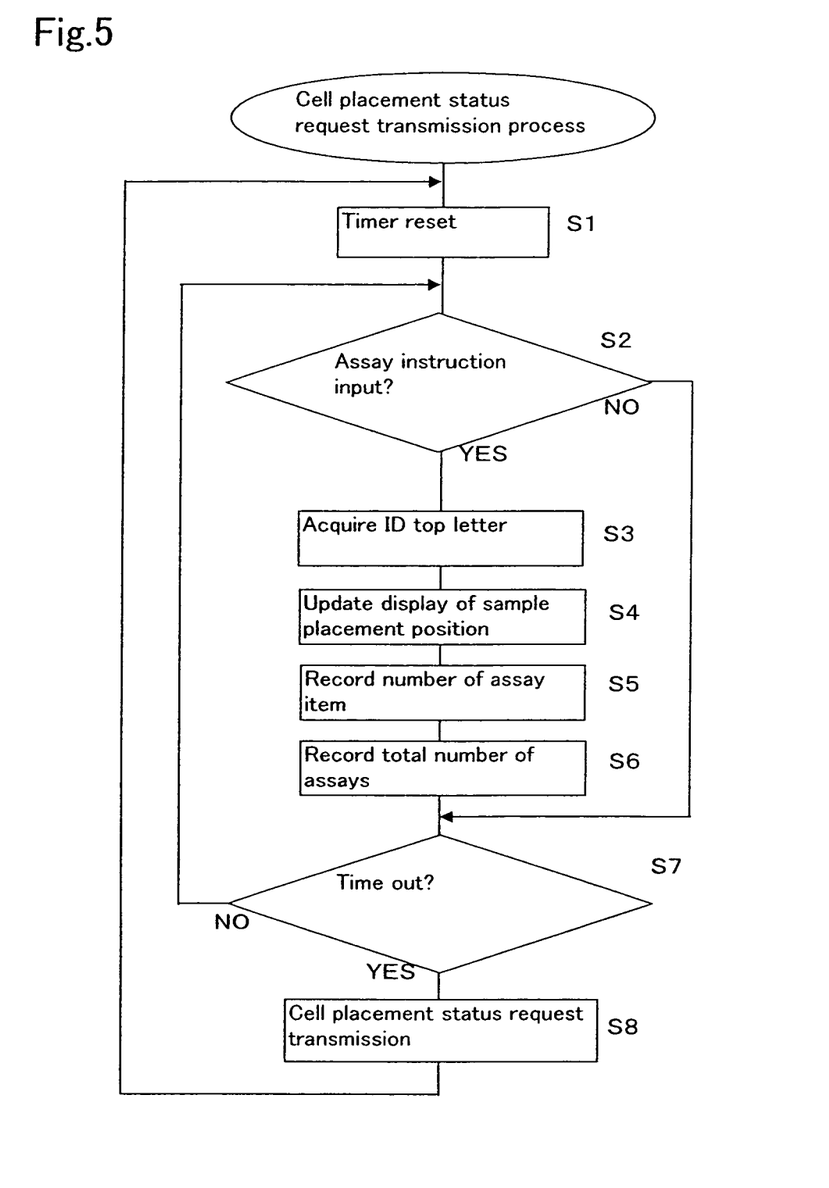
FIG. 5 is a flow chart illustrating the cell placement status request transmission process by the data processing unit of the gene amplification detection device shown in FIG. 1.
Figure 6:
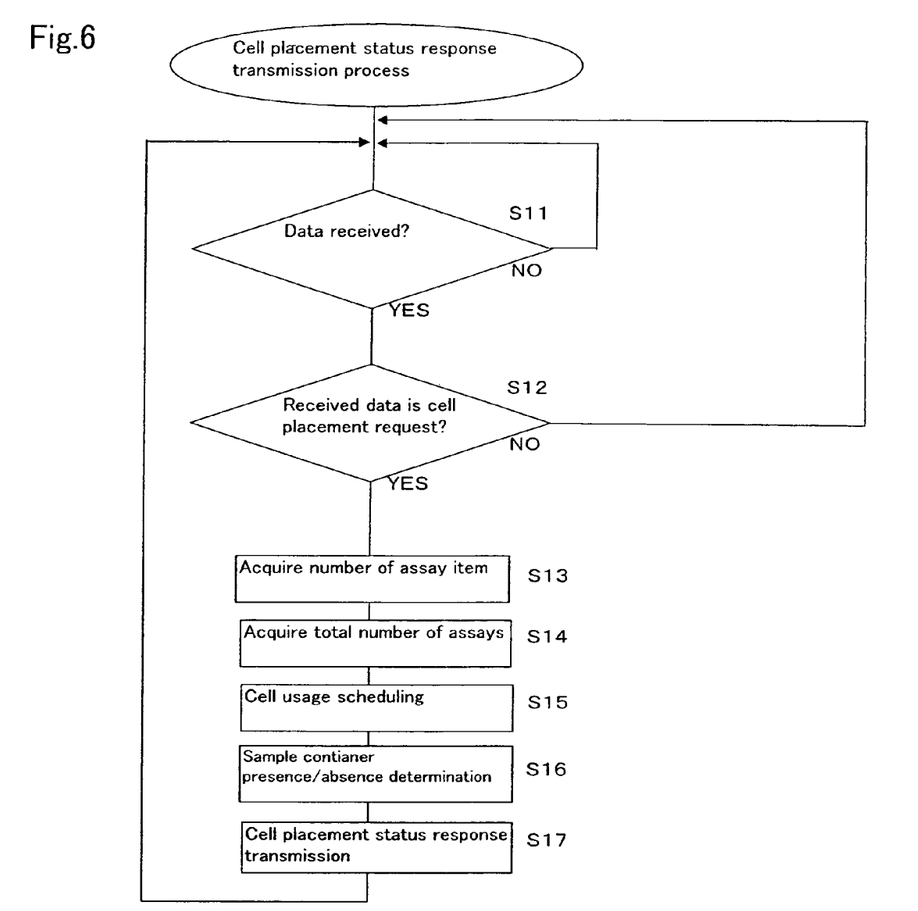
FIG. 6 is a flow chart illustrating the cell placement status response transmission process by the assay unit of the gene amplification detection device shown in FIG. 1.
Figure 7:
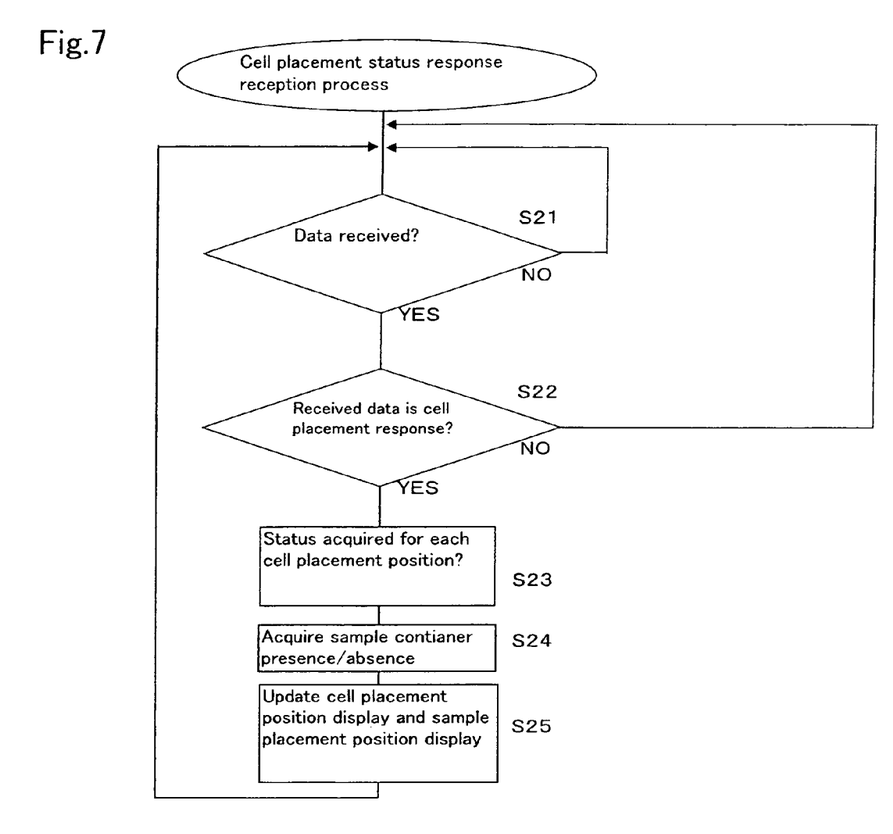
FIG. 7 is a flow chart illustrating the cell placement status response reception process by the data processing unit of the gene amplification detection device shown in FIG. 1.

The processes performed by the data processing unit 102 and assay unit 101 in conjunction with the input assay information on the order input unit 121 is described below with reference to FIGS. 5 through 7. Processing in the data processing unit 102 is performed by the controller 102d, and processing in the assay unit 101 is performed by the controller 80. First, the cell placement status request transmission process executed by the controller 102d of the data processing unit 102 is described with reference to FIG. 5.

Directly after the cell placement status request transmission process starts, a process is executed for setting a timer in step S1. Then, in step S2, a determination is made as to whether or not assay information has been input to the order input unit 121, that is, whether or not there is ID information and the like input via the ID input unit 121a and input from the enter key of the keyboard 102a. When it is determined in step S2 that there is assay information input, then, in step S3, a process is executed to acquire the top letter of the ID input in the ID input unit 121a. Then, in step S4, the display of the sample placement position is updated on the sample placement display 126 based on the acquired top letter. In this way the letter [S] is updated at sample placement positions 1 through 4 on the sample placement position display 126 in correspondence with the sample 001 through sample 004. The background of the sample placement position display 126 is white in step S4 based on the sample placement position input in step S2.

In step S5, the number (1 trough 3) of assay item corresponding to the set group is stored in the memory of the controller 102d. Since the two assay item CK19 and β-actin are set in group (B-CK) in the example of FIG. 4, [2] is stored in memory as the assay item number. In step S6, the total number of assays is calculated and stored in memory. The total number of assays is calculated by totaling the number of assays set using the pull-down menu 121c for the respective samples.

In step S7, a determination is made as to whether or not the timer has timed out. When it is determined that the timer has timed out in step S7, then in step S8, data (cell placement status request) requesting acquisition of the placement status of the detection cells 65 and sample containers 22 are transmitted to the assay unit 101. The data requesting acquisition of the placement status sent to the assay unit 101 includes the total number of assays acquired in step S6 and the number of assay item acquired in step S5. When step S8 is executed, the routine returns to the process of step S1 and the timer is reset.

When it is determined that the timer has not timed out in step S7, the routine returns to step S2. When it is determined that assay information has not been input in step S2, the routine advances to step S7.

The cell placement status response transmission process executed by the assay unit 101 is described below with reference to FIG. 6. In step S11, data reception is awaited. When data are received, a determination is made in step S12 as to whether or not the received data is a cell placement status request. When it is determined that the received data is a cell placement status request in step S12, then in step S13 the number of assay item included in the cell placement status request (acquired in step S5) is obtained, and the total number of assays included in the cell placement status request (calculated in step S6) is obtained. Then, in step S15, a schedule is created for the use of the detection cells 65 based on the total number of assays and the number of assay item.

Figure 9:
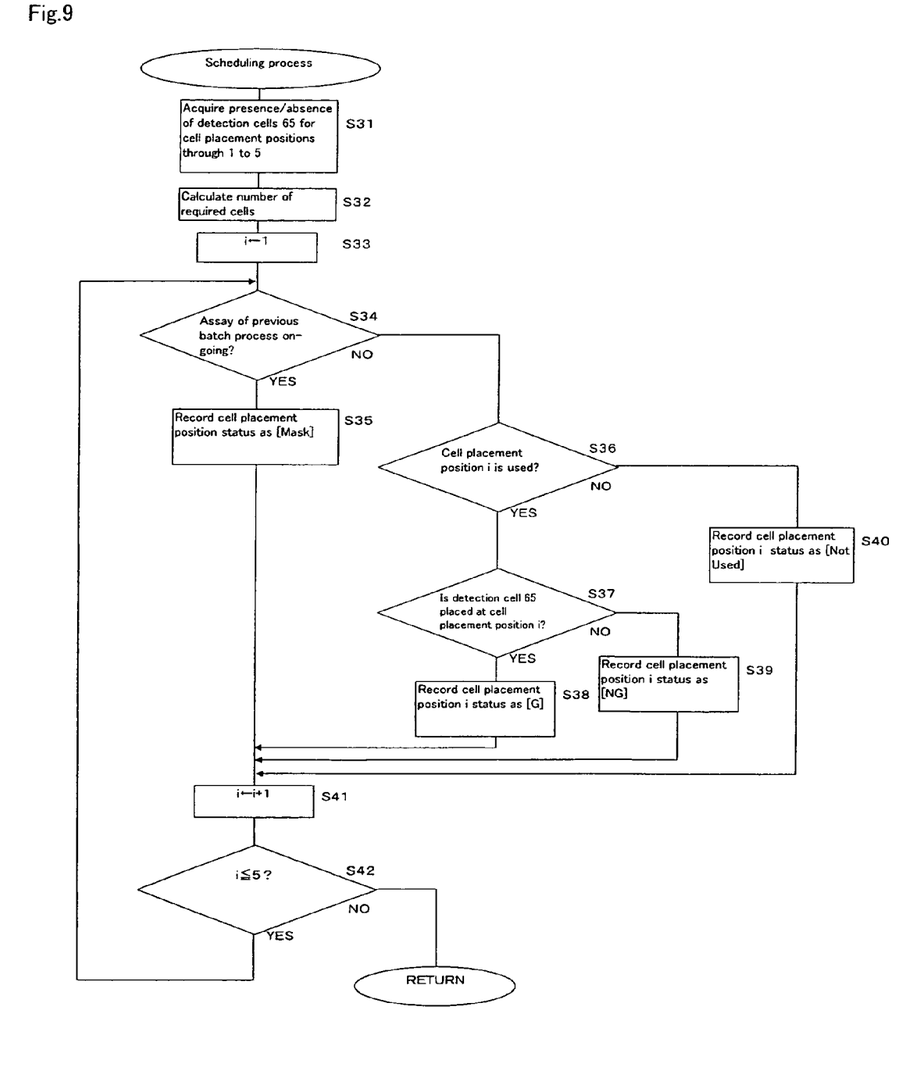
FIG. 9 is a flow chart illustrating the scheduling process by the data processing unit of the gene amplification detection device shown in FIG. 1.

The scheduling process of step S15 is described below using FIG. 9.

In step S31, the presence/absence of the detection cell 65 was obtained for the respective reaction detection blocks 60a of the cell placement positions 1 through 5 based on the intensity of the light received by the photodiode photoreceptor 62b, and the information is stored in the memory 80a. The presence/absence of the detection cell 65 is determined by comparing the intensity of the light received by the photodiode photoreceptor 62b with a predetermined value stored beforehand in the memory 80b, and determining that a detection cell 65 is placed (detection cell present) when the intensity of the light is less than the predetermined value, and determining that a detection cell is not placed (detection cell absent) when the intensity of the light is equal to or greater than the predetermined value.

In step S32, the number of required cells is calculated. The number of required cells is calculated using equation (1) below.

Number of required cells={(number of assay item)× (total number of assays)−(number of assay item unchecked on the item selection unit 121d)}÷2  (1)

The number of required cells is set at an integer by rounding off the decimal point.

For example, when the total number of assays is [4] and the number of assay item is [2], equation (1) gives 2×4÷2, and it is determined that four detection cells 65 including two cells 66a are required. In a further example, when the total number of assays is [4] and the number of assay item unchecked in the item selection unit 126 is [3], equation (1) gives (2×4−3)÷2=2.5, and the 2.5 is rounded up, and the determination is that three detection cells 65 including two cells 66a are required.

In step S33, [1] is entered in "i" as the initial value. In step S34, the gene amplification detection device 100 determines whether or not a previous batch process is being assayed. If the assay is on-going, then in step S35, the cell placement position i is determined to be in the [mask] state and is stored in the memory 80b. Thereafter the process advances to step S41. When the gene amplification detection device 100 is not performing an assay in step S34, a determination is made in step S36 as to whether or not the reaction detection block 60a at cell placement position i is being used. This determination compares "i" with the calculated number of required cells of step S32, and when the "i" is greater than the number of required cells, the cell placement position i is determined to be not in use, whereas the cell placement position i is determined to be in use when "i" is equal to or less than the number of required cells.

When it is determined that the reaction detection block 60a of the cell placement position i is used, then a determination is made in step S37 as to whether or not the detection cell 65 is placed in the reaction detection block 60a of cell placement position i based on the presence/absence of the detection cell 65 in the reaction detection block 60a of the cell placement position i stored in the memory 80b in step S31.

When it is determined that a detection cell 65 is placed in the reaction detection block 60a of the cell placement position i, then it is determined that the reaction detection block 60a of the cell placement position i is a [G] state and stored in the memory 80b in step S38. The process then advances to step S41.

When it is determined in step S37 that a detection cell 65 is not placed in the reaction detection block 60a of the cell placement position i, it is determined that the reaction detection block 60a of the cell placement position i is a [NG] state and stored in the memory 80b in step S39. Then the process advances to step S41.

When it is determined in step S36 that the reaction detection block 60a of the cell placement position i is not being used, it is determined that the reaction detection block 60a of the cell placement position i is in a [Not Used] state and stored in the memory 80b. The process advances to step S41.

In step S41, i+1 is entered for "i". In step S42, a determination is made as to whether or not "i" is equal to or less than 5; when "i" is equal to or less than 5, the process returns to step S34. When "i" is greater than 5, the scheduling process ends, and the routine moves to the process of step S16 (FIG. 6).

[Mask] represents a state in which the cell placement status cannot be determined because a previous batch process is on-going; [G] represents a state in which both the use of the reaction detection block 60a of the cell placement position i is scheduled and the detection cell 65 need not be placed because the detection cell 65 is being placed; [NG] represents a state in which the detection cell 65 must be placed because a detection cell 65 is not placed although the use of the reaction detection block 60a of the cell placement position i is scheduled; and [Not Used] represents a state in which the detection cell 65 need not be placed because the use of the reaction detection block 60a of the cell placement position i is not scheduled.

In step S16 (FIG. 6), a process (sample container presence/absence) is executed for determining whether or not a sample container 22 is placed in the five sample container holes 21a. In this step, a determination is made as to whether or not the five microswitches 21c are ON; sample containers 22 are determined to be placed in the sample container hole 21a when the microswitch 21c is ON.

In step S17, the cell placement status response is sent to the data processing unit 102. The cell placement status response includes the cell placement status in the reaction detection block 60a (Mask, G, NG, and Not Used), and information on the presence/absence of the sample containers 22 for the respective sample placement positions of the sample container holes 21a.

When it is determined in step S12 that the received data is not a cell placement status request, the process returns to step S11.

The cell placement status response reception process executed by the data processing unit 102 is described below with reference to FIG. 7. First, in step S21, data reception is awaited. In step S22, a determination is made as to whether or not the received data is the cell placement status response. When the received data is the cell placement status response in step S22, then in step S23 the status of the reaction detection block 60a of the respective cell placement positions is obtained. In step S24, the presence/absence of the sample containers 22 is obtained for the sample container holes 21a of the respective sample placement positions.

In step S25, the cell placement position displays 125a through 125e and the sample placement position display 126 are updated based on the data obtained in steps S23 and S24.

The cell placement position displays 125a and 125b display [G] in the example of FIG. 4, thus there is scheduled use of the detection cells 65 in the reaction detection block 60a of the cell placement position 1 corresponding to the cell placement position display 125a and the cell placement position 2 corresponding to the cell placement display 125b, and, the detection cells 65 need not be placed because the detection cells 65 are being placed at the reaction detection block 60a of the cell placement position 1 and 2. Furthermore, the cell placement position displays 125a and 125b are displayed in green.

Since the cell placement position displays 125c and 125d display [NG], the detection cells 65 must be placed because detection cells have not yet been placed although the use of the reaction detection block 60a of the cell placement position 3 corresponding to the cell placement position display 125c and the cell placement position 4 corresponding to the cell placement position display 125d are scheduled. Furthermore, the cell placement position displays 125c and 125d are displayed in red.

Since the cell placement position display 125e is displayed in gray, there is no need to place the detection cell 65 because there is no scheduled use of the detection cell 65 in the reaction detection block 60a of the cell placement position 5 corresponding to the cell placement position display 125e.

The display of the cell placement position display 125e in gray indicates the [Not Used] status of the cell placement position 5.

In step S25, it is determined that the sample containers 22 are being placed, and the sample placement positions with ID input are displayed with a green background on the sample placement position display 126.

When the received data is not the cell placement status response in step S22, the process returns to step S21.

In the present embodiment, the user confirms the placement status of the detection cells 65, and determines whether or not the detection cells 65 must be placed based on the updated display of the cell placement status of the reaction detection blocks 60a in step S25. In the screen shown in FIG. 4, detection cells 65 must be placed at the reaction detection blocks 60a of the cell placement positions 3 and 4 corresponding to the cell placement positions displays 125c and 125d displaying [NG] (red), therefore detection cells 65 are placed in the corresponding reaction detection blocks 60a (reaction detection blocks 60a which are third and fourth counting from the inner side of the device).

In this way when step S15 is again executed, it is determined that detection cells 65 are being placed in the reaction detection blocks 60a of the cell placement positions 3 and 4, and the cell placement status is updated from [NG] to [G]. Then, in step S17, the cell placement status response is sent to the data processing unit 102. Then, the controller 102d of the data processing unit 102 acquires status of the reaction detection blocks 60a of the cell placement positions 3 and 4 in step S23, and update the displays of the cell placement position displays 125c and 125d from [NG] (red) to [G] (green) in step S25. In this way the detection cell 65 is properly placed and the start of the assay is enabled.

Thereafter, the user uses the mouse 102b to click the assay start tab 127 shown in FIG. 4. In this way the assay operation is started in the assay unit 101.

When the user clicks the assay start tab 127, the gene amplification detection device 100 sends an assay start instruction from the data processing unit 102 to the assay unit 101, and the assay unit 101 starts the assay operation. The gene amplification detection device 100 does not start the assay operation even when the user clicks the assay start tab 127 if [NG] or [Mask] is displayed on any of the cell placement displays 125a through 125e.

When the user clicks the assay start tab 127 when [NG] is displayed on any of the cell placement displays 125a through 125e, the data processing unit 102 displays a message instructing that a detection cell 65 should be placed in the reaction detection block 60a on the display 102c.

When the operation of the assay unit 101 starts, first, the arm 11 of the dispensing mechanism 10 is moved from the initial position to the tip holder 40 by the transfer device 70, as shown in FIG. 2, and thereafter two syringe units 12 of the dispensing mechanism 10 are lowered. In this way pipette tips 41 are automatically installed on the tips of the nozzles of the two syringe units 12 when the tips of the nozzles on the two syringe units 12 are pressed into the top opening of the pipette tips 41. After the two syringe units 12 have been lifted, the arm 11 of the dispensing mechanism 10 is moved in the X-axis direction by the transfer unit 70 above the two primer reagent containers 32a which contain the CK19 and β-actin primer reagents and are placed in the reagent container placement platform 31. Then, the tips of the two pipette tips 41 installed in the two syringe units 12 are inserted into the liquid surface of the primer reagents CK19 and β-actin within the primer reagent containers 32a by the syringe units 12 by lowering the two syringes 12. Next, the CK19 and β-actin primer reagent within the primer reagent containers 32a are suctioned by the syringes 12.

After suctioning the primer reagent and lifting the two syringes 12, the arm 11 of the dispensing mechanism 10 is moved by the transfer unit 70 above the reaction detection block 60a positioned at the cell placement position 1 on the innermost side (front inner side of the device). At the innermost reaction detection block 60a, the two pipette tips 41 installed in the two syringe units 12 are respectively inserted into the two cells 66a of the detection cell 65. The two primer reagents CK19 and β-actin are discharged into the two cells 66a by the syringes 12.

After the primer reagents are discharged and the two syringe units 12 are lifted, the arm 11 of the dispensing mechanism 10 is moved in the X-axis direction above the tip disposal unit 50 by the transfer unit 70. The pipette tips 41 are disposed of in the tip disposal unit 50. Specifically, the pipette tips 41 are inserted into the two tip disposal holes 50a (refer to FIG. 3) of the tip disposal unit 50 by lowering the two syringes 12. In this state, the pipette tips 41 are moved to the bottom of the channel 50b by moving the arm 11 of the dispensing mechanism 10 in the Y-axis direction by the transfer unit 70. Then, the flange on the top surface of the pipette tips 41 contacts the bottom surface of the bilateral sides of the channel 50b so as to receive a downward force from the bottom surface of the channel 50b, and the pipette tips 41 are automatically detached from the nozzle of the two syringes 12. In this way the pipette tips 41 are disposed in the tip disposal unit 50.

Then, the arm 11 of the dispensing mechanism 10 is again moved to the tip holder 40 by the transfer unit 70. Thereafter, at the tip holder 40, two new pipette tips 41 are automatically installed on the tips of the nozzles of the two syringes by the previously described operation. The arm 11 of the dispensing mechanism 10 is moved by the transfer unit 70 in the X-axis direction above the enzyme reagent container 32b which contains both CK19 and β-actin reagents and placed in the reagent container placement platform 31, and thereafter the enzyme reagent within the enzyme reagent container 32b is suctioned. Specifically, one syringe unit 12 is lowered to a position above the enzyme reagent container 32b and enzyme reagent is suctioned, and subsequently this syringe unit 12 is lifted. Thereafter, the arm 11 of the dispensing mechanism 10 is moved in the Y-axis direction by the transfer unit 70 so that the other syringe unit 12 is positioned above the same enzyme reagent container 32b. Then, the other syringe unit 12 is lowered and the enzyme reagent is suctioned from the same enzyme reagent container 32b, and thereafter the other syringe unit 12 is raised. The arm 11 of the dispensing mechanism 10 then is moved above the reaction detection block 60a on the innermost side by the transfer unit 70, and the CK19 and β-actin enzyme reagent is discharged into the two cells 66a of the detection cell 65. After the enzyme reagent has been discharged, the arm 11 of the dispensing mechanism 10 is moved above the tip disposal unit 50 by the transfer unit 70, and the pipette tips 41 are disposed.

The arm 11 of the dispensing mechanism 10 is again moved to the tip holder 40 by the transfer unit 70, and subsequently two new pipette tips 41 are automatically installed on the tips of the nozzles of the two syringe units 12. Then, the arm 11 of the dispensing mechanism 10 is moved by the transfer unit 70 in the X-axis direction above the sample container 22 which contains a sample and is placed in the sample container placement platform 21, and subsequently the sample in the sample container 22 is suctioned by the same operation as the enzyme reagent suction operation.

Thereafter, the arm 11 of the dispensing mechanism 10 is moved by the transfer unit 70 above the reaction detection block 60a on the innermost side, and subsequently the two syringe units 12 are lowered and identical samples are discharged into the two cells 66a of the detection cell 65. When dispensing the primer reagent, enzyme reagent, and sample, the temperature of the liquid in the detection cell 65 is maintained at approximately 20° C. Thereafter, the arm 11 of the dispensing mechanism 10 is moved above the tip disposal unit 50 by the transfer unit 70, and the pipette tips 41 are disposed.

After the primer reagent, enzyme reagent, and sample have been discharged into the cell 66a, the cover-closing operation of the cover 67a of the detection cell 65 is performed. After the cover-closing operation is completed, the temperature of the liquid in the cell 66a is increased from approximately 20° C. to approximately 65° C. to amplify the nucleic acid (mRNA) via the LAMP (gene amplification) reaction. Then, the target gene is detected using a nephelometric method to analyze the turbidity, which is produced by magnesium pyrophosphate generated in conjunction with amplification of the nucleic acid. Specifically, the controller 102d monitors the turbidity of the liquid contained in the detection cell 65 in real time by means of the intensity of the light received by the photodiode photoreceptor 62b shown in FIG. 3.

As described above, the target gene is detected by the reaction detection block 60a positioned on the innermost side. When assay information is input as shown in FIG. 4, the reaction detection blocks 60a second through fourth from the inner side may sequentially perform similar operations of target gene detection to that performed by the reaction detection block 60a on the innermost side. The detection operation ends when the target gene detection operation performed by the fourth reaction detection block 60a ends. Thereafter, the user grips the handle 67c of the detection cell 65 and disposes of the four detection cells 65.

Figure 8:
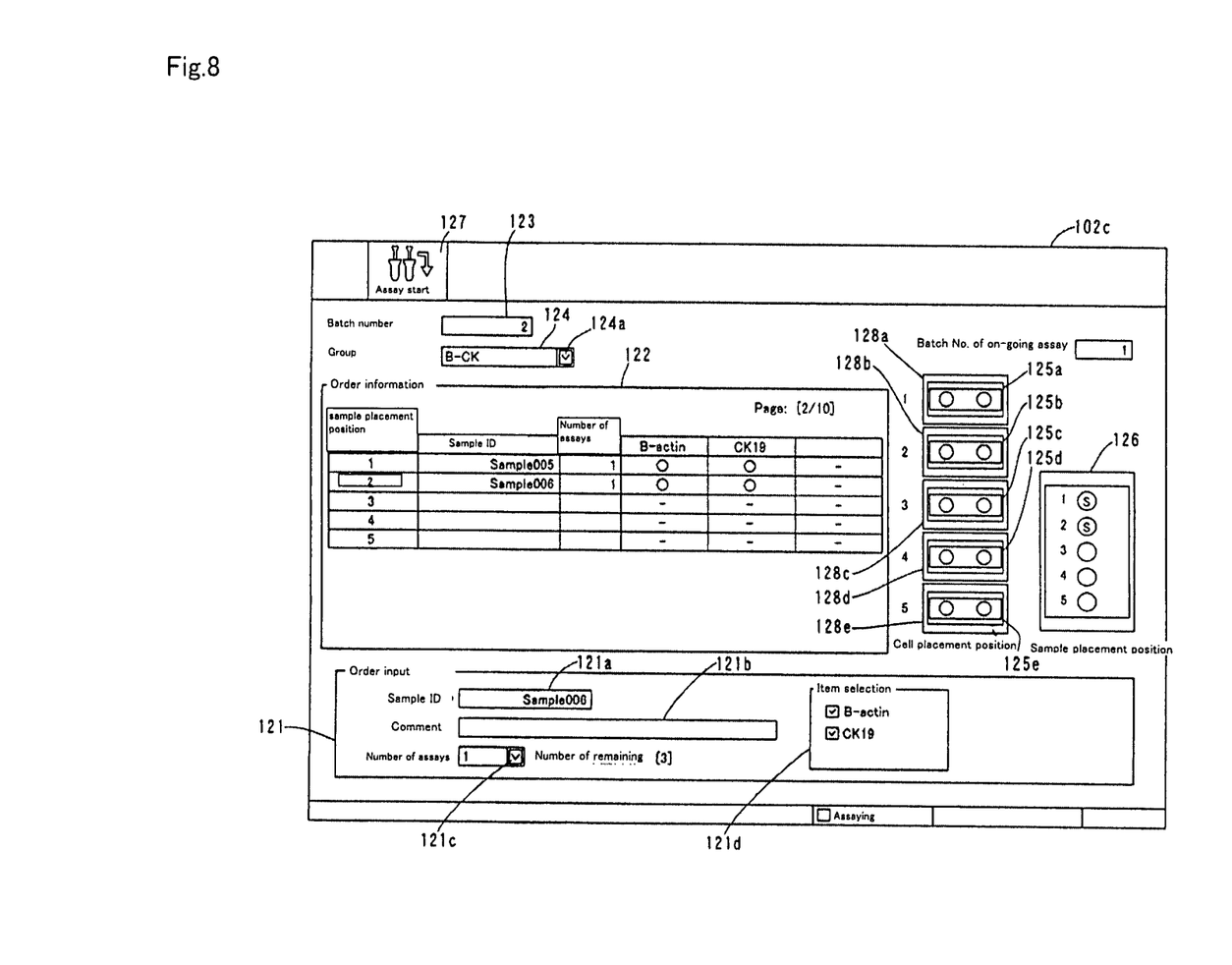
FIG. 8 shows details of the screen during assay which is displayed on the display of the data processing unit of the gene amplification detection device shown in FIG. 1.

When a previous batch process assay is on-going, the [Mask] state is determined in which the status of the cell placement position cannot be determined in step S35. In this case, the cell placement position displays 125a through 125e of the display 102c show Mask 128a~128e, as shown in FIG. 8. It is possible to input assay information for the current batch process even during an on-going assay of a previous batch process, as shown in the screen of FIG. 8. In the screen of FIG. 8, the IDs "Sample 005" and "Sample006" and the number of assays for one cycle are input, and the B-CK group is selected for assaying the two item of CK19 and β-actin.

In the present embodiment, the user can easily confirm the placement position of the detection cells 65 since the placement positions required for the placement of the detection cells 65 of the container holder 60 are displayed on the display 102c by providing the controllers 80 and 102d for acquiring the status of the detection reaction blocks 60a based on the assay information input through the keyboard 102a and mouse 102b and output of the photodiode photoreceptor 62b, and by providing the display 102c for displaying the status of the reaction detection block 60a acquired by the controllers 80 and 102d. Furthermore, since whether or not a detection cell 65 is actually placed at the specified cell placement position of the reaction detection block 60a can be detected by providing the LED light source 62a and photodiode photoreceptor 62b for detecting whether or not a detection cell 65 is placed in the reaction detection block 60a, the user can determine when a detection cell 65 is placed in the proper cell placement position of the reaction detection block 60a.

In the present embodiment, the user can easily confirm the placement status of the reaction detection blocks 60a since colors corresponding to the detection cell 65 placement status (green for [G], red for [NG], and gray for [Not Used]) are displayed in addition to the abbreviations ([G], [NG]) indicating the detection cell 65 placement status on the cell placement position displays 125a through 125e.

In the present embodiment, the detection block has a simplified structure compared to separate detection block for detecting the presence/absence of the detection cell 65, and detecting the turbidity of the liquid contained in the detection cell 65 since the presence/absence of the detection cell 65 and the turbidity of the liquid contained in the detection cell 65 can be detected using a single turbidity detection unit 62 having an LED light source 62a and photodiode photoreceptor 62b.

In the present embodiment, the controller 80 of the assay unit 101 determines the presence/absence of the detection cell 65 based on the light received by the photodiode photoreceptor 62b, and the controller 102 of the data processing unit 102 analyzes the turbidity if the liquid in the detection cell 65 based on the light received by the photodiode photoreceptor 62b, and processing speed is improved since processing is performed by the two controllers 80 and 102d.

The embodiment described above is in all aspects an example and should not be considered as limiting the present invention. The scope of the invention is expressed in the scope of the claims and not by the description of the embodiment, and includes all modifications and equivalent meanings within the scope of the claims.

For example, although the analyzer of the present invention is described by way of example applied to a gene amplification detection device for amplifying a target nucleic acid using the LAMP method in the above embodiment, the present invention is not limited to this arrangement inasmuch as the present invention may also be applied to gene amplification detection devices (nucleic acid detection devices) for amplifying a target nucleic acid using a polymerase chain reaction (PCR method) and ligase chain reaction (LCR method). Furthermore, the present invention is broadly applicable to analyzers other than gene amplification detection devices.

The present embodiment has been described by way of example of detecting the presence/absence of a detection cell 65 and detecting the turbidity of the liquid contained in the detection cell 65 using a single turbidity detection unit 62 having a LED light source 62a and photodiode photoreceptor 62b, the present invention is not limited to this arrangement inasmuch as the detection of the presence/absence of the detection cell 65 also may be detected based on the intensity of light obtained from a separate detection unit than the detection of the turbidity of the liquid contained in the detection cell 65.

In the present embodiment, letters representing an abbreviation ([G], [NG]) indicating the placement status of a reaction detection block 60a, and colors corresponding to the detection cell 65 placement status (green for [G], red for [NG], and gray for [Not Used]) are displayed on the cell placement position displays 125a through 125e, however, the present invention is not limited to this arrangement inasmuch as only one may be displayed among the abbreviations and patterns representing the placement status of the reaction detection blocks 60a, and colors corresponding to the placement status of the reaction detection blocks 60a. In the present embodiment, the presence/absence of a detection cell 65 is determined by the controller 80, and the analysis of the turbidity of the liquid in the detection cell 65 is determined by the controller 102d, however, these determinations also may be made by one controller.

In the embodiment, the placement status of the sample container in the sample container placement hole 21a, and the placement status of the detection cell 65 in the reaction detection block 60a are displayed on the display 102c, however, the present invention is not limited to this arrangement inasmuch as the placement status of the reagent containers in the primer reagent container hole 31a and the enzyme reagent container hole 31b also may be displayed on the display 102c.

In the embodiment, the presence/absence of the detection cell 65 is accomplished using a turbidity detection unit 62 including an LED light source 62a and photodiode photoreceptor 62b, however, the present invention is not limited to this arrangement inasmuch as the presence/absence of the detection cell 65 also may be detected by providing a microswitch within the hole of the detection cell placement position 61a and having the microswitch turn ON when a detection cell 65 is placed therein.

In the embodiment, the assay operation is started when the user clicks the assay start tab 127, however, the present invention is not limited to this arrangement inasmuch as an assay start switch may be provided on the assay unit 101 to start the assay operation when the user presses this start switch.

In the embodiment, the reaction unit 61 is disposed between the LED light source 62a and the photodiode photoreceptor 62b, and the controller 80 determines the presence/absence of the detection cell 65 based on the intensity of the light received by the photodiode photoreceptor 62b, however, the present invention is not limited to this arrangement inasmuch as the LED light source 62a and photodiode photoreceptor 62b may be provided on one side wall of the reaction unit 61 and the controller 80 may determine the presence/absence of the detection cell 65 based on the intensity of the light received by the photodiode photoreceptor 62b. In this case, since the intensity of the light received by the photodiode photoreceptor 62b increases via reflected light when a detection cell 65 is in place, the controller 80 may compare the light received by the photodiode photoreceptor 62b with a predetermined value stored beforehand in the memory 80b, and determines the presence of the detection cell 65 when the light intensity is greater than the predetermined value, and determine the absence of the detection cell 65 when the light intensity is less than the predetermined value.

The above embodiment is described by way of example in which the five sample placement positions and cell placement positions are displayed regardless of the presence/absence of ID input and presence/absence of scheduled use of the detection cell 65, however, the present invention is not limited to this arrangement inasmuch as only the sample placement positions for which an ID has been input may be displayed on the sample position display 126, and only the cell placement position of scheduled use may be displayed on the cell placement position displays 125a through 125e.

In the embodiment, the detection cell 65 has the two container parts, however, the present invention is not limited to this arrangement inasmuch as the detection cell 65 may have single container part.

In the embodiment, the reaction detection block 60a has two detection cell placement positions 61a, the present invention is not limited to this arrangement inasmuch as the reaction detection block 60a may have single detection cell placement positions 61a.

What is claimed is:
1. A detection apparatus comprising:
an input unit configured for receiving assay information relating to assays of a sample;

an assay unit configured for assaying the sample comprising a nucleic acid in accordance with the assay information, the assay unit comprising:
- a sample container holder for placing a sample container comprising the sample;
- a reagent container holder for placing a reagent container comprising a reagent;
- a reaction container holder for placing reaction containers, wherein the reaction container holder comprises a plurality of reaction container placement positions for placing the reaction containers;
- a plurality of detectors for detecting whether or not a reaction container is placed at a reaction container placement position; and
- a dispensing mechanism for preparing an assay sample comprising the sample and the reagent in the reaction container placed at the reaction container holder by respectively aspirating the sample from the sample container placed at the sample container holder and the reagent from the reagent container placed at the reagent container holder, and discharging the sample and the reagent into the reaction container; wherein:
- the assay unit amplifies the nucleic acid in the assay sample in the reaction container placed at the reaction container holder;

a display; and a controller programmed to
- determine a number of reaction containers to be used based on the assay information received by the input unit;
- determine a reaction container placement position on which a reaction container should be placed based on the determined number of reaction containers to be used and detection results of the detectors;
- generate a reaction container placement status screen in response to an input provided by at least one of the plurality of detectors, wherein the reaction container placement status screen represents that a reaction container should be placed at the determined reaction container placement position; and
- control the display to display the reaction container placement status screen.

2. The detection apparatus of claim 1, wherein the reaction container holder comprises a reaction container placement position for placing the reaction container; wherein the detector comprises detectors comprise a light source and a receiver for receiving light emitted from the light source; and wherein the reaction container placement position is between the light source and the receiver.

3. The detection apparatus of claim 1,
wherein the input unit is further configured for receiving an instruction to start an assay of a sample; and
wherein the controller controls the display to output a message to place a reaction container when the input unit has received the instruction to start an assay and the display is displaying the reaction container placement status screen representing that a reaction container should be placed at the determined reaction container placement position.

4. The detection apparatus of claim 1,
wherein the input unit is further configured for receiving an instruction to start an assay of a sample; and
wherein the assay unit does not start a sample assay when the input unit has received the instruction to start an assay and the display is displaying the reaction container placement status screen representing that a reaction container should be placed at the determined reaction container placement position.

5. The detection apparatus of claim 1, wherein:
the controller further determines a second reaction container placement position on which a reaction container is being placed based on detecting results of the detectors; and
the reaction container placement status screen further represents that a reaction container need not be placed at the determined second reaction container placement position.

6. The detection apparatus of claim 1, wherein:
the controller further determines a third reaction container placement position which is not used based on the assay information received by the input unit; and
the reaction container placement status screen further represents that a reaction container need not be placed at the determined third reaction container placement position.

7. The detection apparatus of claim 1, wherein:
the controller further determines a second reaction container placement position on which a reaction container is being placed and a third reaction container placement position which is not used based on the assay information received by the input unit and the detecting results of the detectors; and
the reaction container placement status screen further represents that a reaction container need not be placed at the determined second and third reaction container placement positions.

8. The detection apparatus of claim 1, wherein:
the sample container holder comprises a plurality of sample container placement positions for placing the sample containers;
the controller further determines a sample container placement position on which a sample container should be placed based on the assay information received by the input unit; and
the controller further generates a sample container placement status screen, wherein the sample container placement status screen represents that a sample container should be placed at the determined sample container placement position; and controls the display to display the sample container placement status screen.

* * * * *